US007889898B2

(12) United States Patent
Chakraborty et al.

(10) Patent No.: US 7,889,898 B2
(45) Date of Patent: Feb. 15, 2011

(54) SYSTEM AND METHOD FOR SEMANTIC INDEXING AND NAVIGATION OF VOLUMETRIC IMAGES

(75) Inventors: Amit Chakraborty, East Windsor, NJ (US); Bogdan Georgescu, Princeton, NJ (US); Nemanja Petrovic, New York, NY (US); Paolo Favaro, Edinburgh (GB); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1045 days.

(21) Appl. No.: 11/532,556

(22) Filed: Sep. 18, 2006

(65) Prior Publication Data
US 2007/0127798 A1 Jun. 7, 2007

Related U.S. Application Data

(60) Provisional application No. 60/717,804, filed on Sep. 16, 2005.

(51) Int. Cl.
*G06K 9/00* (2006.01)
(52) U.S. Cl. ..................................... 382/128
(58) Field of Classification Search ................. 382/128, 382/154, 159, 131, 132; 705/3; 600/407, 600/443, 447, 444, 449
See application file for complete search history.

(56) References Cited

U.S. PATENT DOCUMENTS

| 6,106,466 | A  | * | 8/2000 | Sheehan et al. | ............. 600/443 |
| 2003/0013951 | A1 | * | 1/2003 | Stefanescu et al. | .......... 600/407 |
| 2006/0074721 | A1 | * | 4/2006 | Cotthingham et al. | .......... 705/3 |
| 2007/0036414 | A1 | * | 2/2007 | Georgescu et al. | .......... 382/128 |

\* cited by examiner

*Primary Examiner*—Anand Bhatnagar
*Assistant Examiner*—Claire Wang (57) ABSTRACT

A method for navigating digital medical images includes providing a digitized patient medical image of a structure of interest in a patient, using a pre-trained classifier to segment the structure of interest from the image, creating links from the structure of interest to a corresponding structure in an anatomical atlas, receiving a query to view the structure of interest, parsing the query to identify one or more keywords from noun phrases in the query, mapping a keyword to a corresponding structure in the anatomical atlas, wherein the anatomical atlas structure is associated with a link to the corresponding structure in the patient image, and following the link to display said patient structure of interest.

24 Claims, 5 Drawing Sheets

SYSTEM AND METHOD FOR SEMANTIC INDEXING AND NAVIGATION OF VOLUMETRIC IMAGES

CROSS REFERENCE TO RELATED UNITED STATES APPLICATIONS

This application claims priority from "Semantic Indexing and Navigation of Volumetric Images", U.S. Provisional Application No. 60/717,804 of Chakraborty, et al., filed Sep. 16, 2005, the contents of which are incorporated herein by reference.

TECHNICAL FIELD

This invention is directed to annotating and linking volumetric digital medical images.

DISCUSSION OF THE RELATED ART

The diagnostically superior information available from data acquired from current imaging systems enables the detection of potential problems at earlier and more treatable stages. Given the vast quantity of detailed data acquirable from imaging systems, various algorithms must be developed to efficiently and accurately process image data. With the aid of computers, advances in image processing are generally performed on digital or digitized images.

Digital images are created from an array of numerical values representing a property (such as a grey scale value or magnetic field strength) associable with an anatomical location points referenced by a particular array location. The set of anatomical location points comprises the domain of the image. In 2-D digital images, or slice sections, the discrete array locations are termed pixels. Three-dimensional digital images can be constructed from stacked slice sections through various construction techniques known in the art. The 3-D images are made up of discrete volume elements, also referred to as voxels, composed of pixels from the 2-D images. The pixel or voxel properties can be processed to ascertain various properties about the anatomy of a patient associated with such pixels or voxels. Computer-aided diagnosis ("CAD") systems play a critical role in the analysis and visualization of digital imaging data.

The efficient visualization of volumetric datasets is important for many applications, including medical imaging, finite element analysis, mechanical simulations, etc. The 3-dimensional datasets obtained from scanning modalities such as computed tomography (CT), magnetic resonance imaging (MRI), positron emission tomography (PET), ultrasound (US), etc., are usually quite complex, and contain many different objects and structures. In many instances, it is difficult to distinguish between two different objects that have similar intensity values in the imaged data. In other cases, the region of interest to the user is surrounded either partially or completely by other objects and structures. There is often a need to either remove an obstructing surrounding object, or to keep the region of interest and remove all other objects.

In recent years, the acquisition and visualization of volumetric images have gained immense popularity, especially in the medical world. Advances in imaging and computing technology are creating an explosion of data in image form. However, the ability to quickly analyze this information is limited by inefficiencies in image display. The ability to rapidly access and display large image sets would considerably improve analysis and conceptualization of information contained within the images. Moreover, with this widespread usage of large data volumes comes the problem of efficient navigation to the point of interest. For large volume datasets acquired within the medical domain, this is almost impossible without proper annotation and linking. For making proper diagnosis, clinicians need to be able to see the image volume from the right view and angle. But this is non-trivial and requires a systematic approach in order to be feasible. In order to develop a satisfying image navigation system, it is desirable to have tools to construct a semantic bridge between the user and the image volume.

SUMMARY OF THE INVENTION

Exemplary embodiments of the invention as described herein generally include methods and systems for a novel combination of database-guided segmentation and hyperlinking for realizing an image indexing/annotation scheme and a query system, which allow the user to quickly navigate to the desired location. This approach includes: (1) identifying important structures and their corresponding views in the image; (2) linking them to a query system; and (3) developing an easy navigation mechanism. A system and method according to an embodiment of the invention provides a way to easily navigate complex volumetric data within the clinical setting. Image volumes are first acquired and a learning based system is trained to extract objects of interest. This information is stored in an XML metafile. The input volumes are then linked to an annotated phantom data file. A query/navigation module allows the intended clinical users to navigate to the objects of interest in the volume data of choice via the phantom.

According to an aspect of the invention, there is provided a method for navigating digital medical images including the steps of providing a digitized patient medical image of a structure of interest in said patient, said image comprising a plurality of intensities corresponding to a domain of points on an 3-dimensional grid, using a pre-trained classifier to segment said structure of interest from said image, and creating links between said structure of interest to a corresponding structure in an anatomical atlas, wherein said links are adapted to facilitating navigation through said patient image to said structure of interest.

According to a further aspect of the invention, the method comprises saving the segmentation of said structure of interest and said links to said corresponding structure in a metafile.

According to a further aspect of the invention, the method comprises registering said image to a mean shape of said structure of interest.

According to a further aspect of the invention, the method comprises computing one or more feature vectors from said structure of interest, wherein said feature vectors are used as input to said classifier.

According to a further aspect of the invention, each said feature vector comprises a set of coefficients from an expansion of said feature vector in terms of Haar basis functions.

According to a further aspect of the invention, the classifier segments said structure of interest by classifying said structure into a predefined category.

According to a further aspect of the invention, the links are created based on rules that specify the source and destination of said links.

According to a further aspect of the invention, the links are hyperlinks.

According to a further aspect of the invention, the method comprises creating links between said structure of interest and a patient medical report.

According to a further aspect of the invention, the method comprises providing a query to view said structure of interest, parsing said query to identify one or more keywords from noun phrases in said query, mapping a keyword to a corresponding structure in said anatomical atlas, wherein said anatomical atlas structure is associated with at least one of said links to the corresponding structure in said patient image, and following said at least one link to display said patient structure of interest.

According to a further aspect of the invention, the classifier is trained by providing a plurality of training images of said structure of interest, for each image, annotating said structure of interest wherein a 3-D mesh of points is formed, aligning each mesh wherein a registration transformation between each pair of training images is calculated, calculating a mean shape of said structure of interest from said aligned meshes, generating positive and negative training samples from said plurality of training images, calculating one or more feature vectors for each structure of interest in said plurality of training images, and using boosting one said feature vectors to train a classifier that can categorize each said structure of interest in said training set into a pie-defined category based on the size and complexity of each said structure of interest.

According to a further aspect of the invention, a positive training sample is a structure of interest that can be perfectly aligned with said mean shape of said structure of interest, and a negative training sample is a structure of interest that cannot be perfectly aligned with said mean shape of said structure of interest.

According to a further aspect of the invention, the boosting comprises AdaBoost.

According to another aspect of the invention, there is provided a program storage device readable by a computer, tangibly embodying a program of instructions executable by the computer to perform the method steps for navigating digital medical images.

DETAILED DESCRIPTION OF THE PREFERRED EMBODIMENTS

Exemplary embodiments of the invention as described herein generally include systems and methods for annotating and linking images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume, or more generally, a function from $R^n$ to $R^m$. For example, a color RGBA image volume would be a function from $R^3$ to $R^4$. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Figure 1:
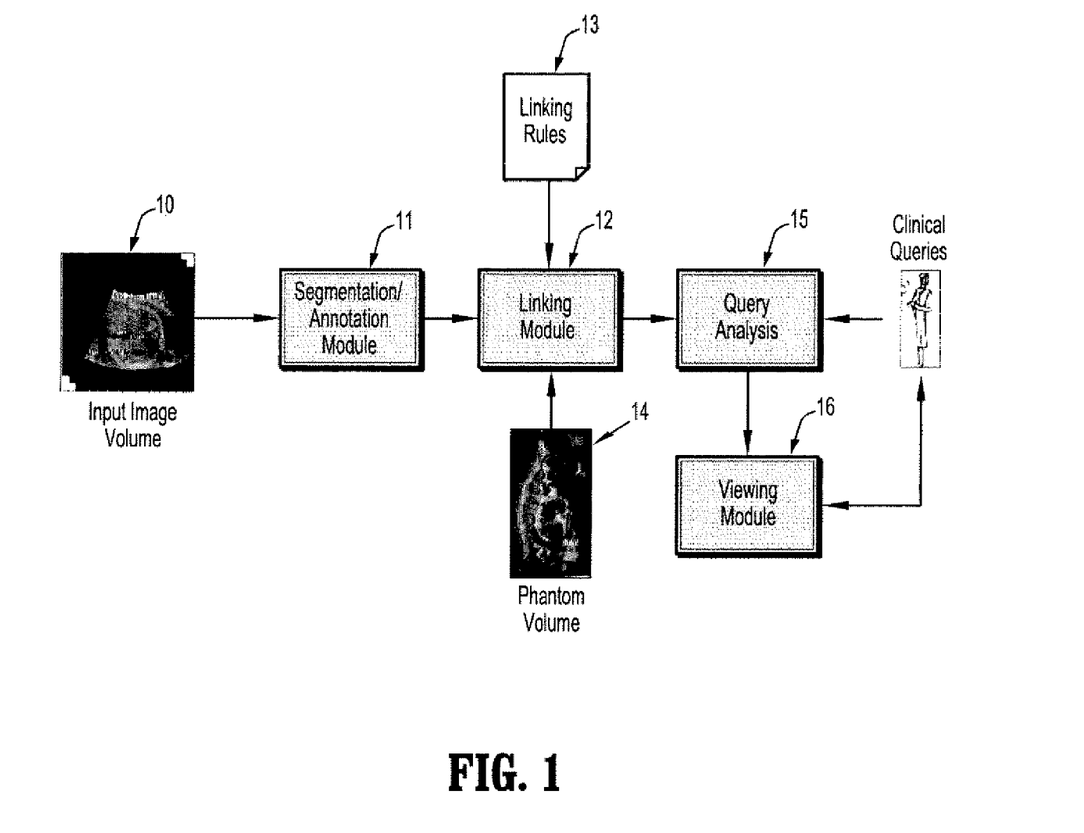
FIG. 1 is a schematic block diagram of a system for annotating and linking images, according to an embodiment of the invention.

A schematic block diagram of a system for annotating and linking images, according to an embodiment of the invention, is shown in FIG. 1. When new volumetric image data 10 is acquired, a database-guided segmentation/annotation module 11 is invoked to segment/annotate it. This module identifies the important structures and their corresponding views in the image. Next, these structures are linked by a linking module 12 to a phantom volume 14 using automated linking mechanisms, including linking rules 13. The phantom volume is an idealized model for which hyperlinks have been defined, and is also referred to as an anatomical atlas. The linking rules are described in greater detail herein below. The linked structures/phantom-volume support an efficient query system. Query information from the clinician can be used by query analysis module 15 to properly orient the volume and display the right information in the viewing module 16, presenting an easy mechanism for navigation.

According to an embodiment of the invention, a database-guided learning-based approach is used for segmenting objects of interest. It uses expert annotation of structures of interest. Since direct computation of features from volumetric data is computationally expensive, according to an embodiments of the invention, the volume can be divided into 2D slices and these slices are used instead. Note, however, that embodiments of the invention are not limited to using 2D slices, and according to other embodiments of the invention, automatic indexing can process 3D volumetric data as well.

Figure 2:
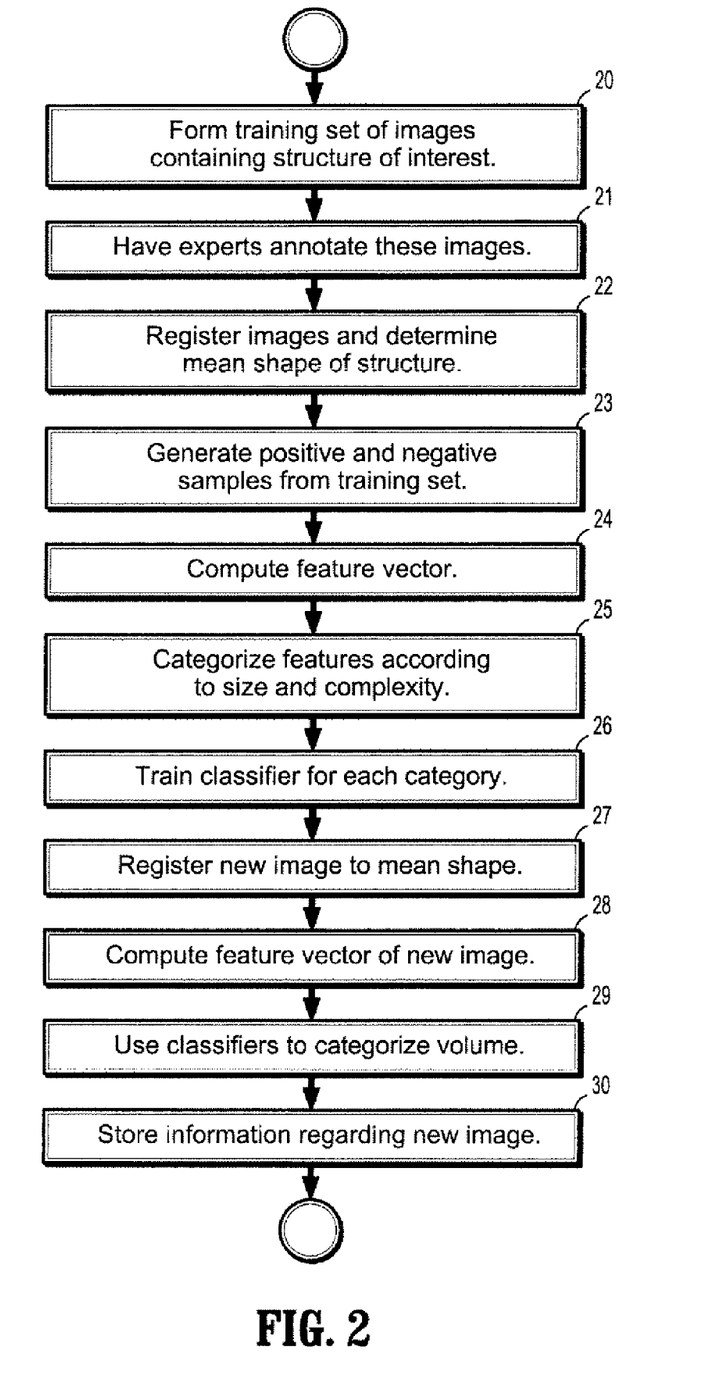
FIG. 2 is a flow chart of a learning-based segmentation method according to an embodiment of the invention.

FIG. 2 is a flow chart of a learning-based segmentation method according to an embodiment of the invention. Referring now to the figure, since a training based approach is being used, the first training step 20 involves identifying volumes for a particular structure of interest. These volumes form a training set. For each of these volumes, experts are requested at step 21 to annotate the shapes of interest. According to an embodiment of the invention, the shapes of interest are annotated over 2D slices. According to another embodiment of the invention, the shapes of interest are annotated directly in the 3D volume. In annotating an image volume, a user marks in the input volume either the center of the structure, a diameter of the structure of interest, or the outline/shape of the structure. The last type of annotation can result in a surface shape represented by a mesh. The end result is a plurality of 3D meshes, one for each structure. In addition, an idealized version of the shape/mesh is visualized in the anatomical atlas, and given a new volume, the system can automatically determine the shape. This allows the user to navigate through hyperlinks placed on the anatomical atlas, as described below.

The meshes are aligned with each other at step 22 computing a registration transformation between each pair of volumes. According to an embodiment of the invention, a registration transformation can be computed by first registering the principal axis in each mesh and then estimating the appropriate scaling and translation to minimize the Euclidean distance between them. Once the volumes of the training set have been registered, the mean shape is computed to be the average of all the training volumes when properly registered. Positive and negative training samples are generated from the training sets at step 23. When a mesh is perfectly (or almost perfectly) registered to the mean shape, it is labeled as positive, and when a mesh is not well aligned due to imperfect registration parameters, it is labeled as negative. Thus, positive and negative samples can be generated from the same training set.

Once a transformation is determined for each volume that registers that volume to the mean shape and their associated labels, a list of simple features is computed at step 24 for each volume using the corresponding transformation. Each feature can be represented by an expansion in terms of Haar basis functions, and for each feature, a feature vector can be formed that comprises the set of coefficients from the Haar expansion. For a dataset that has been divided into 2D slices, the feature functions are computed from the horizontal and vertical slices of the dataset. Based on the range of shapes represented in the training set, the set of all possible shapes is divided at step 25 into pre-defined categories based on the size and complexity of the shape under consideration, as determined the feature vectors for each shape. At step 26, a boosting technique uses the feature vectors to create the best classifier for categorizing the training set to the set of shapes defined above. The corresponding most informative feature vectors are also identified. An exemplary, non-limiting boosting technique is AdaBoost.

When a new image volume dataset is introduced, the volume is first registered to the mean shape at step 27, and the feature vector is computed at step 28. According to an embodiment of the invention, the feature vector is computed from 2D slices extracted from the new image dataset that correspond to slices extracted from the training volumes. According to another embodiment of the invention, the feature vector is computed directly from the 3D image volume. At step 29, the classifier is used to categorize the new volume into one of the predefined categories and the corresponding object definition is used to segment this volume. The annotation information about the volume, the organ of interest, it's location and the reference to the patient and his/her medical condition is then stored at step 30 in a file. An exemplary, non-limiting file type is an XML file.

As noted earlier, to make a system according to an embodiment of the invention more useful to a clinician, it is desired that the clinician be able to navigate easily to an organ of interest. To facilitate this, hyperlinks can be dynamically created in an automated fashion between the image volumes and a phantom image which is used as a guide for the clinician. Links can also be created between patient specific volumes and their medical reports.

Figure 3:
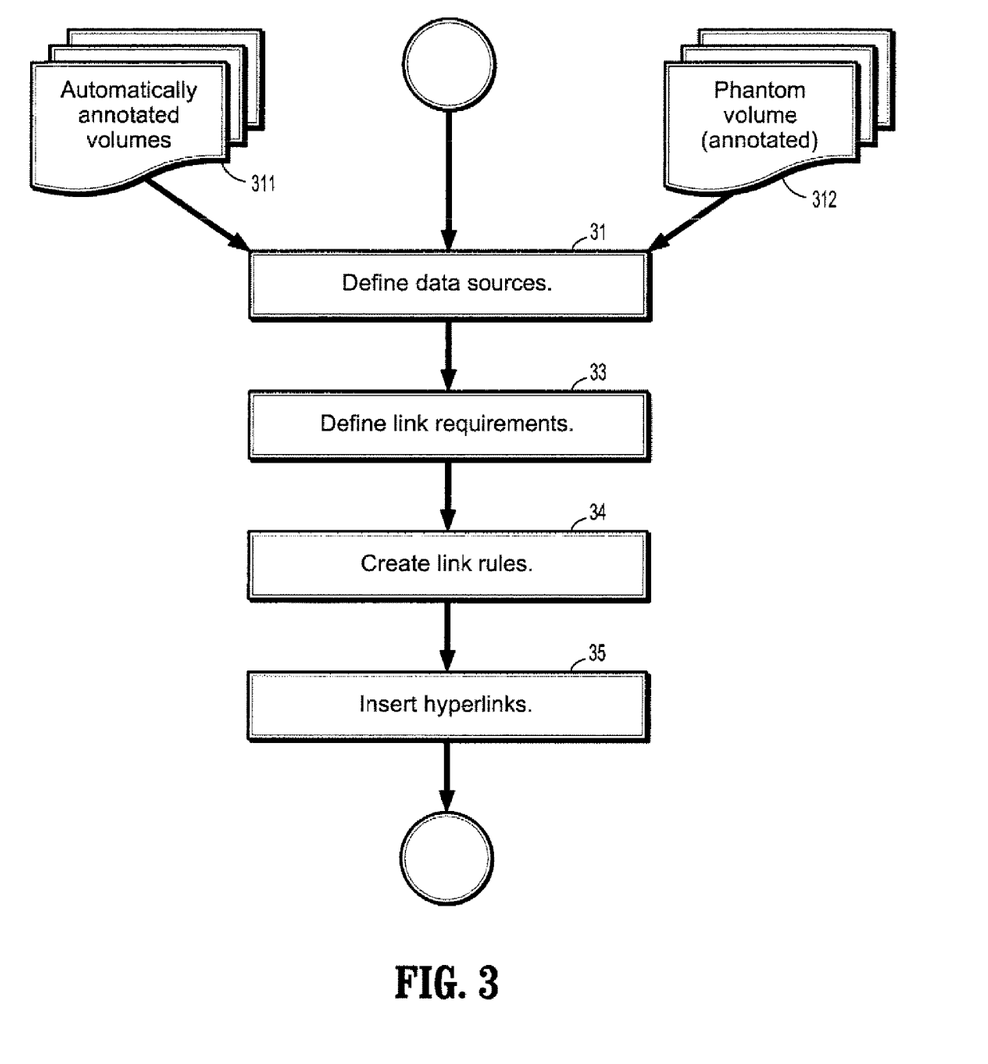
FIG. 3 is a flow chart of a linking mechanism, according to an embodiment of the invention.

FIG. 3 is a flow chart of a dynamic linking mechanism according to an embodiment of the invention. Referring now to the figure, the data sources would be defined at step 31. In an exemplary, non-limiting case, the data sources would be a new, incoming patient image volume data 311, and the phantom image 312. The phantom is manually annotated once for all the objects of interest and the information is stored in a metafile, such as an XML file, specific for the phantom. The patient image data is automatically segmented according to a method such as that illustrated in FIG. 2, and the information stored in a corresponding file, such as an XML metafile, as described above.

At step 33, link requirements are defined. Defining link requirements involves understanding what objects or structures need to be linked to other objects or structures, taking into account the underlying biology. For example, for cardiac links, certain standard cut planes through the heart itself are useful because a user might be interested in quickly navigating to one of these standard views, for example to perform measurements. In this case, there would be a requirement for a link between each standard cut plane in the patient heart image and the corresponding standard cut planes in the phantom image. The source image would be the phantom, and the destination image would be the patient image. Link rules are created at step 34 from the patterns and requirements that define the nature and type of link. These link rules can be created in a pre-defined rule language that can be understood by a parser, such as the XML parser.

```
An exemplary, non-limiting link-rule XML file is as
    follows.
<?xml version="1.0" encoding="UTF-8" ?>
<template name="Link Rules">
    <linkrule id="ATCV" name="Atlas GIF to cardiac view GIF">
        <source context="AtlasFigure">
            <variable name="aiuFile" type="pathexpr"
                regexpr="(.+)(\.aiu)">
                //docheader/@file</variable>
            <variable name="imageFile" type="string">
                $aiuFile(1)$ + ".gif"</variable>
            <variable name="sourceContent" type="pathexpr">
                //aiudoc/anatomy/@name</variable>
        </source>
        <destination context="cardiacView">
            <variable name="aiuFile" type="pathexpr"
                regexpr="(.+)(\.aiu)">
                //docheader/@file</variable>
            <variable name="imageFile" type="string">
                $aiuFile(1)$ + ".gif"</variable>
            <variable name="destContent" type="pathexpr">
                //aiudoc/anatomy/@name/view1</variable>
        </destination>
    </linkrule>
</template>
```

The source is the phantom image, referred to as "Atlas", and the destination is the 3D cardiac image of the patient. The links are created from the metadata extracted for both the files. In this non-limiting, case, the metadata files have the extension ".aiu". Both of these metadata files are organized hierarchically with the root being called "aiudoc", which for a simple case may be the anatomical image and its name. In the non-limiting example illustrated above, to be linked, the names of the organs, which are variables, have to match. However, more complex patterns than that illustrated can be supported. In this non-limiting example, a fixed view is used for the destination, however, this view selection could also be a variable as well. In addition to the anatomical information, the link rules can also specify traditional identifying information such as the patient name and so on in the destination. Finally, at step 35, a hyperlinker is run which parses the XML files and creates and the appropriate link and inserts it into the patient data volume. The hyperlinks enable a user who has clicked on the source file at a particular location to be taken to the corresponding 3D image view of the patient image.

Figure 4:
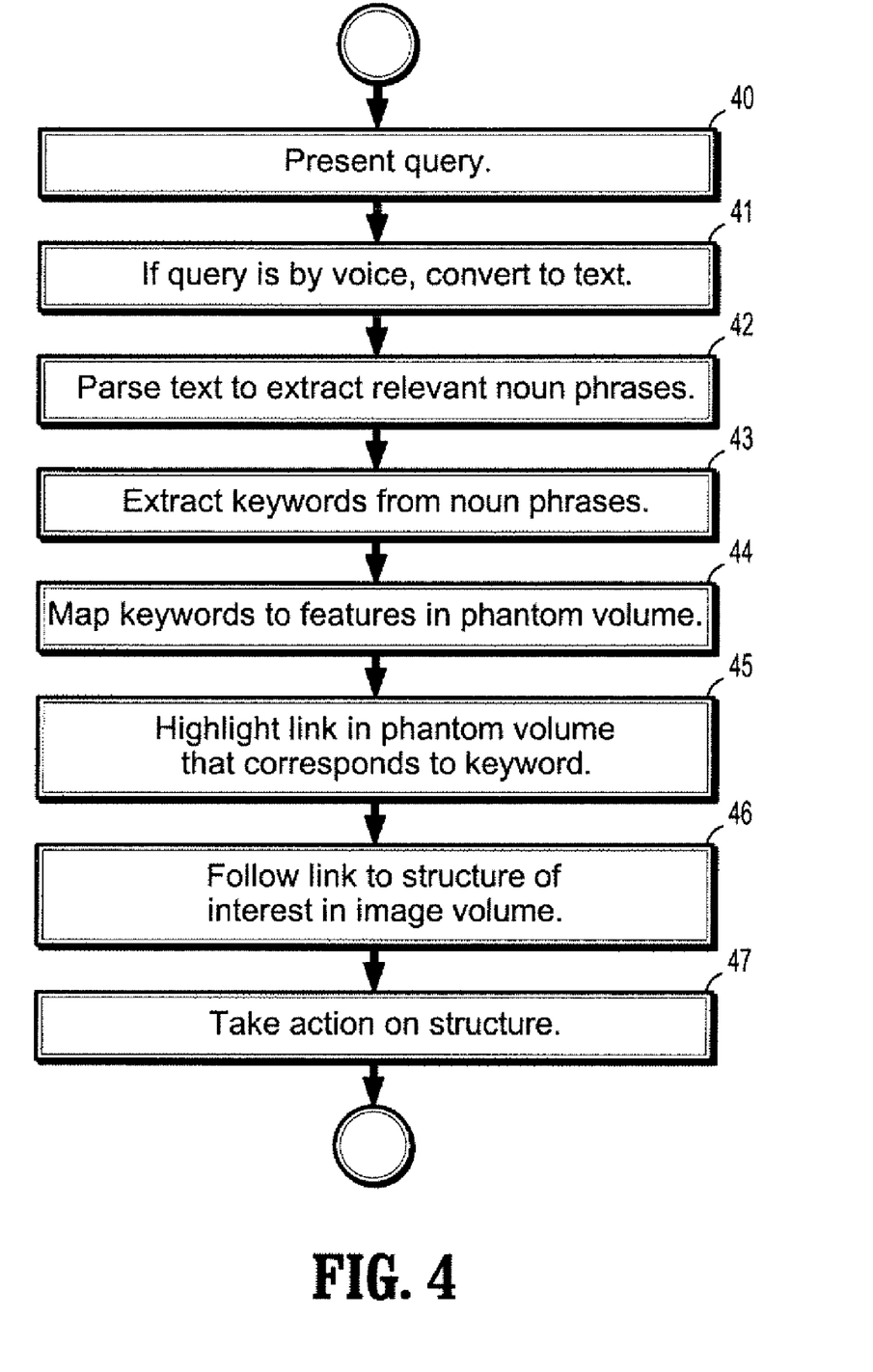
FIG. 4 is a flow chart for querying and viewing a medical image volume, according to an embodiment of the invention.

According to an embodiment of the invention, querying and navigating through medical data volumes can be facilitated through written and voice activated queries. A flow chart for querying and viewing a medical image volume is depicted in FIG. 4. Referring now to the figure, a query is presented at step 40. A query can be posed either as text or via voice. If a query is voice dictated to the system, it is converted at step 41 to text using a voice recognition system. An exemplary, non-limiting, query is "Show me the fetal head." Next, at step 42, the text of the query is parsed to extract the relevant noun phrases. In the example provided, a noun phrase would be "fetal head". Important keywords are extracted at step 43 from these noun phrases, such as the name of the patient, the organ of interest, etc. Again, in the example provided, exemplary keywords would be "fetal" and "head". The keywords are mapped at step 44 to the phantom volume. A viewer displays the phantom volume to a user on a computer monitor. For example, a phantom volume of a fetus could be presented to the user, who could then click on the head to be presented with a view of the fetal head. Another exemplary phantom model would be a drawing of the heart, or a principled model of the heart. The user could then click on a part of the heart, such as one of the standard cut planes, and the system automatically links to and retrieves and displays to the user the corresponding view from the actual patient anatomical data. The viewer of the phantom volume is able to load the associated XML metafile as well. The associated link on the phantom that corresponds to the object of interest is highlighted at step 45. The user can then follow the link at step 46 either by voice command or by mouse clicking to view the appropriate volume with the object of interest highlighted. At step 47, the clinical user can take an appropriate action, such as taking measurements of the object of interest.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 5:
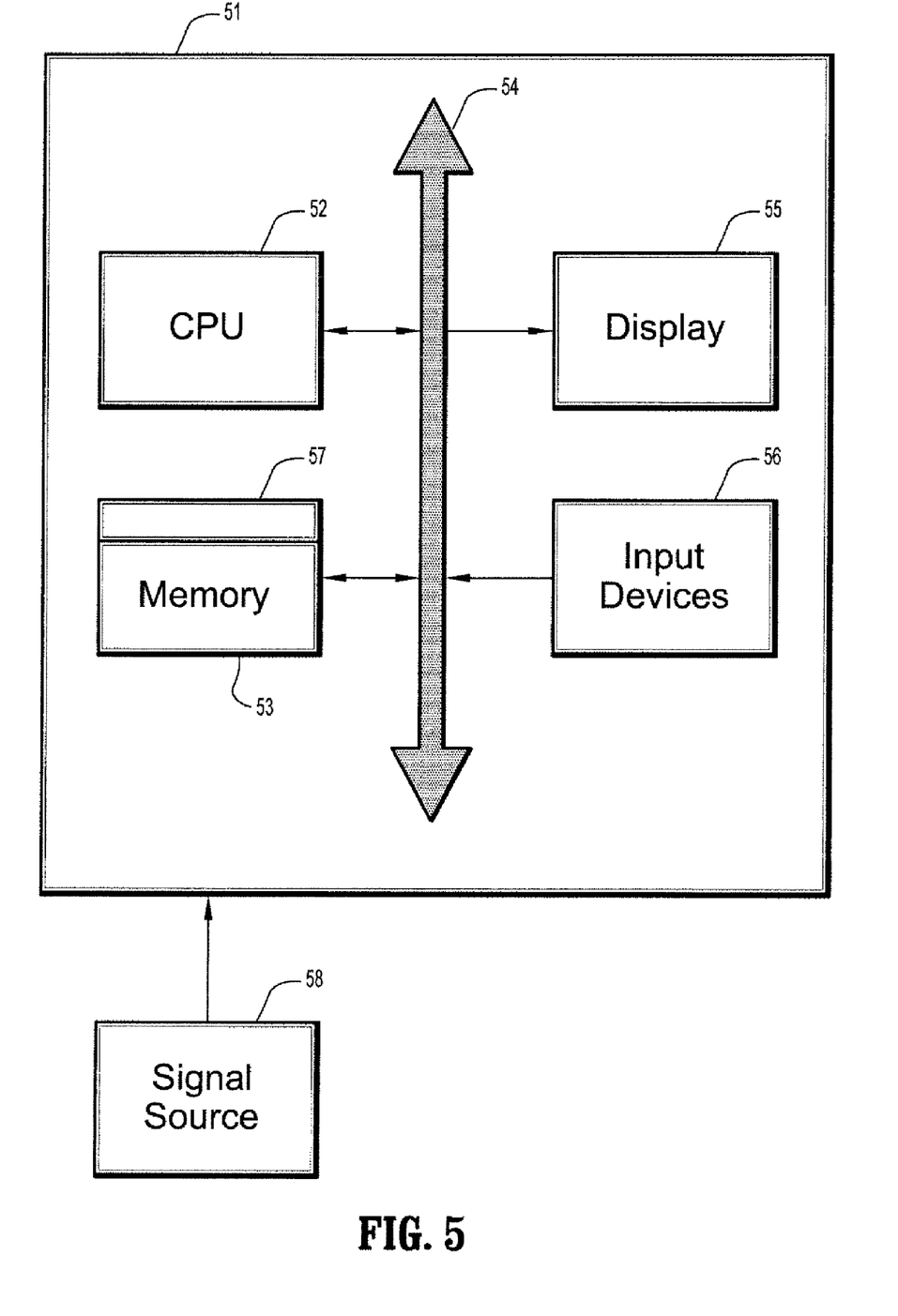
FIG. 5 is a block diagram of an exemplary computer system for implementing a system for annotating and linking images, according to an embodiment of the invention.

FIG. 5 is a block diagram of an exemplary computer system for implementing a database-guided segmentation and hyperlinking method for image indexing and annotation, according to an embodiment of the invention. Referring now to FIG. 5, a computer system 51 for implementing the present invention can comprise, inter alia, a central processing unit (CPU) 52, a memory 53 and an input/output (I/O) interface 54. The computer system 51 is generally coupled through the I/O interface 54 to a display 55 and various input devices 56 such as a mouse and a keyboard. The support circuits can include circuits such as cache, power supplies, clock circuits, and a communication bus. The memory 53 can include random access memory (RAM), read only memory (ROM), disk drive, tape drive, etc., or a combinations thereof. The present invention can be implemented as a routine 57 that is stored in memory 53 and executed by the CPU 52 to process the signal from the signal source 58. As such, the computer system 51 is a general purpose computer system that becomes a specific purpose computer system when executing the routine 57 of the present invention.

The computer system 51 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for navigating digital medical images comprising the steps of:
providing a digitized patient medical image of a structure of interest in said patient, said image comprising a plurality of intensities corresponding to a domain of points on an 3-dimensional grid;
using a pre-trained classifier to categorize the structure of interest into one of a set of predefined categories to segment said structure of interest from said image; and
creating links between said structure of interest to a corresponding structure in an anatomical atlas, wherein said links are adapted to facilitating navigation through said patient image to said structure of interest, wherein said links are created based on rules that specify the source and destination of said links.

2. The method of claim 1, further comprising saving the segmentation of said structure of interest and said links to said corresponding structure in a metafile.

3. The method of claim 1, further comprising registering said image to a mean shape of said structure of interest.

4. The method of claim 1, further comprising computing one or more feature vectors from said structure of interest, wherein said feature vectors are used as input to said classifier.

5. The method of claim 4, wherein each said feature vector comprises a set of coefficients from an expansion of said feature vector in terms of Haar basis functions.

6. The method of claim 1, wherein said links are hyperlinks.

7. The method of claim 1, further comprising creating links between said structure of interest and a patient medical report.

8. The method of claim 1, further comprising:
receiving a word-based query to view said structure of interest;
parsing said query to identify one or more keywords from noun phrases in said query;
mapping a keyword to a corresponding structure in said anatomical atlas, wherein said anatomical atlas structure is associated with at least one of said links to the corresponding structure in said patient image; and
following said at least one link to display said patient structure of interest.

9. The method of claim 1, wherein said classifier is trained by providing a plurality of training images of said structure of interest;
for each image, annotating said structure of interest wherein a 3-D mesh of points is formed;

aligning each mesh wherein a registration transformation between each pair of training images is calculated;

calculating a mean shape of said structure of interest from said aligned meshes;

generating positive and negative training samples from said plurality of training images;

calculating one or more feature vectors for each structure of interest in said plurality of training images; and using boosting on said feature vectors to train a classifier that can categorize each said structure of interest in said training set into a pre-defined category based on the size and complexity of each said structure of interest.

10. The method of claim 9, wherein a positive training sample is a structure of interest that can be perfectly aligned with said mean shape of said structure of interest, and a negative training sample is a structure of interest that cannot be perfectly aligned with said mean shape of said structure of interest.

11. The method of claim 9, wherein said boosting comprises AdaBoost.

12. A method for navigating digital medical images comprising the steps of:

providing a digitized patient medical images of a structure of interest in a patient, said image comprising a plurality of intensities corresponding to a domain of points on an 3-dimensional grid;

using a pre-trained classifier to segment said structure of interest from said image;

creating links between said structure of interest to a corresponding structure in an anatomical atlas;

receiving a word-based query to view said structure of interest;

parsing said query to identify one or more keywords from noun phrases in said query;

mapping a keyword to a corresponding structure in said anatomical atlas, wherein said anatomical atlas structure is associated with at least one of said links to the corresponding structure in said patient image; and following said at least one link to display said patient structure of interest.

13. The method of claim 12, wherein said classifier is trained by providing a plurality of training images of said structure of interest;

for each image, annotating said structure of interest wherein a 3-D mesh of points is formed:

aligning each mesh wherein a registration transformation between each pair of training images is calculated;

calculating a mean shape of said structure of interest from said aligned meshes;

generating positive and negative training samples from said plurality of training images;

calculating a feature vector for each structure of interest in said plurality of training images;

using said feature vector to train a classifier that can categorize each said structure of interest in said training set into a pre-defined category based on the size and complexity of each said structure of interest, wherein said classifier is adapted to segmenting a corresponding structure of interest from a digitized patient medical image not in said training set.

14. A program storage device readable by a computer, tangibly embodying a non-transitory program of instructions executable by the computer to perform the method steps for navigating digital medical images, said method comprising the steps of:

providing a digitized patient medical image of a structure of interest in said patient, said image comprising a plurality of intensities corresponding to a domain of points on an 3-dimensional grid;

using a pre-trained classifier to categorize the structure of interest into one of a set of predefined categories to segment said structure of interest from said image; and creating links between said structure of interest to a corresponding structure in an anatomical atlas, wherein said links are adapted to facilitating navigation through said patient image to said structure of interest, wherein said links are created based on rules that specify the source and destination of said links.

15. The computer readable program storage device of claim 14, the method further comprising saving the segmentation of said structure of interest and said links to said corresponding structure in a metafile.

16. The computer readable program storage device of claim 14, the method further comprising registering said image to a mean shape of said structure of interest.

17. The computer readable program storage device of claim 14, the method further comprising computing one or more feature vectors from said structure of interest, wherein said feature vectors are used as input to said classifier.

18. The computer readable program storage device of claim 17, wherein each said feature vector comprises a set of coefficients from an expansion of said feature vector in terms of Haar basis functions.

19. The computer readable program storage device of claim 14, wherein said links are hyperlinks.

20. The computer readable program storage device of claim 14, the method further comprising creating links between said structure of interest and a patient medical report.

21. The computer readable program storage device of claim 14, the method further comprising:

receiving a word-based query to view said structure of interest;

parsing said query to identify one or more keywords from noun phrases in said query;

mapping a keyword to a corresponding structure in said anatomical atlas, wherein said anatomical atlas structure is associated with at least one of said links to the corresponding structure in said patient image; and following said at least one link to display said patient structure of interest.

22. The computer readable program storage device of claim 14, wherein said classifier is trained by providing a plurality of training images of said structure of interest;

for each image, annotating said structure of interest wherein a 3-D mesh of points is formed;

aligning each mesh wherein a registration transformation between each pair of training images is calculated;

calculating a mean shape of said structure of interest from said aligned meshes;

generating positive and negative training samples from said plurality of training images;

calculating one or more feature vectors for each structure of interest in said plurality of training images; and using boosting on said feature vectors to train a classifier that can categorize each said structure of interest in said training set into a pre-defined category based on the size and complexity of each said structure of interest.

23. The computer readable program storage device of claim 22, wherein a positive training sample is a structure of interest that can be perfectly aligned with said mean shape of said structure of interest, and a negative training sample is a structure of interest that cannot be perfectly aligned with said mean shape of said structure of interest.

24. The computer readable program storage device of claim 22, wherein said boosting comprises AdaBoost.

* * * * *